United States Patent
Barnard

[19]

[11] Patent Number: 6,110,111

[45] Date of Patent: Aug. 29, 2000

[54] SYSTEM FOR QUANTIZING BLADDER DISTENSION DUE TO PRESSURE USING NORMALIZED SURFACE AREA OF THE BLADDER

[75] Inventor: William L. Barnard, Seattle, Wash.

[73] Assignee: Diagnostic Ultrasound Corporation, Redmond, Wash.

[21] Appl. No.: 09/318,378

[22] Filed: May 26, 1999

[51] Int. Cl.$^7$ .................................................. A61B 8/00
[52] U.S. Cl. ............................................................ 600/438
[58] Field of Search .................................... 600/437, 438, 600/458, 460, 459; 606/3

[56] References Cited

U.S. PATENT DOCUMENTS 5,474,071  12/1995  Chapelon et al. ...................... 600/458
5,957,920   9/1999  Baker ........................................ 606/33

Primary Examiner—Marvin M. Lateef
Assistant Examiner—Maulin Patel
Attorney, Agent, or Firm—Jensen & Puntigam, P.S.

[57] ABSTRACT

The apparatus is worn by a user and includes means for automatically scanning the bladder of the user with ultrasound signals. The returning signals are used to calculate the volume of urine in the bladder and also to calculate the actual surface area of the bladder. The theoretical surface area of a spherical bladder having the said calculated volume is then determined. A surface area index (SAI) is then determined as follows:

$$\frac{\text{Surface area (theoretical)}}{\text{Surface area (actual)}} = \text{Surface area index } (SAI)$$

The SAI value is an indication of the roundness of the bladder and hence the pressure within the bladder.

18 Claims, 2 Drawing Sheets

SYSTEM FOR QUANTIZING BLADDER DISTENSION DUE TO PRESSURE USING NORMALIZED SURFACE AREA OF THE BLADDER

TECHNICAL FIELD

This invention relates generally to non-invasive techniques for determining bladder condition, and more specifically concerns the determination of bladder pressure, i.e. the pressure of urine in the bladder.

BACKGROUND OF THE INVENTION

Non-invasive techniques, typically using ultrasound, are well-known for determining bladder volume, i.e. the amount of urine in the bladder. The reliability and accuracy of such ultrasound techniques have been well-documented and they are now well accepted by the medical community. Information concerning bladder volume is used by health professionals in the treatment of bladder dysfunction and to prevent over-filling of the bladder in those cases where there is a permanent or temporary loss of bladder sensation, due to spinal cord injuries and/or postoperative recovery, as well as other reasons.

It is also well-recognized that an important aspect of good bladder health involves prevention of bladder distension. Typically, as bladder pressure increases, due to increase in volume of urine, ultimately leading to the point where bladder distension begins to occur, incontinent episodes will occur because the sphincter muscles are unable to retain the urine in the bladder. On many individuals, the point of incontinence occurs consistently at a particular volume. If this particular volume is known, then incontinent events can be prevented by using information on bladder pressure/distension.

If the bladder continues to fill so that it becomes hyperdistended, renal damage, renal failure and in some cases even death can occur. Hyperdistension, like distension, can be successfully prevented, however, by measuring using bladder distension.

At low bladder volumes, bladder distension information is typically not very useful. As the bladder fills, however, a quantization of bladder distension becomes more useful relative to ascertaining problematic conditions. Bladder distension information is potentially more useful than just straight volume measurements because normal bladder capacity varies widely across the human population. The same volume of urine in two different patients can have very different consequences.

There have been previous attempts to quantize bladder distension, including the use of ultrasound back wall scatter characterization in determining bladder wall thickness. Bladder wall muscles will stretch and thin as the bladder fills. This thinning of the bladder wall can be directly measured by recording backscatter information at various known volumes for a particular patient. Such methods, however, are not particularly reliable or consistent and often do not directly correlate with actual distension of the bladder.

In the present invention, a substantially different approach is taken, directed toward ascertaining the degree of roundness of the bladder as it fills, with increasing roundness being a reliable indication of pressure.

DISCLOSURE OF THE INVENTION

Accordingly, the present invention is an apparatus for automatically determining a bladder volume index value, which provides information concerning the bladder condition of a user, comprising: means for automatically scanning a bladder of a user with ultrasound signals, receiving the ultrasound signals and then calculating therefrom the volume of urine in the bladder of the user; means for automatically calculating an actual surface area of the user's bladder from the returning ultrasound signals; means for automatically determining a theoretical surface area of a sphere having said calculated surface area; and means for determining a surface area index value for the user by dividing the theoretical value of the surface area by the actual value of the surface area.

BEST MODE FOR CARRYING OUT THE INVENTION

Figure 1:
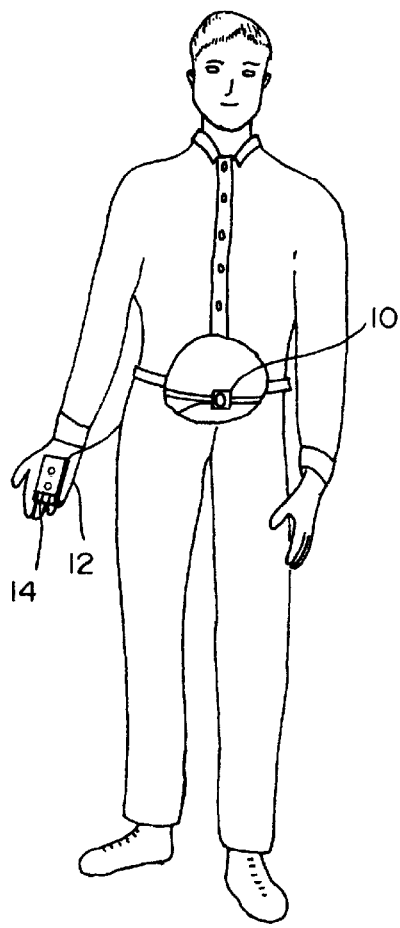
FIG. 1 is a diagram showing use of the present invention on a patient.

The apparatus shown in FIG. 1 includes a conventional ultrasound transducer member 10 which is typically held in position against the body of a user, adjacent the actual position of the bladder within the body. Transducer 10 can be held in that position by a variety of devices, such as a belt or straps.

In operation, transducer 10 transmits an ultrasound signal into the body and then receives the returning signal. Transducer 10 is electrically connected to a control processor 12 which includes ultrasound processing electronics (microprocessor) and software associated therewith. Ultrasound transducer member 10 and control processor unit 12 are used to accomplish the first step in the system of the present invention, namely, determining the volume of the bladder in a non-invasive manner. Two specific techniques for doing so are disclosed in detail in U.S. Pat. No. 4,926,871 to Ganguly et al and U.S. Pat. No. 5,235,985 to McMorrow et al, both of which are either owned or exclusively licensed by the assignee of the present invention. Both of those patents are incorporated by reference herein. Those patents provide detailed explanations of a system for non-invasively transmitting, receiving and processing ultrasound signals relative to the bladder, and then for calculating bladder volume therefrom.

Figure 2:
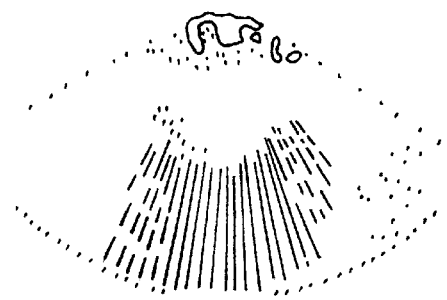
FIG. 2 is an ultrasound diagram showing one scan plane in the imaging of a bladder.

Transducer 10 in operation transmits an ultrasound signal (approximately 2 MHz in the embodiment shown) into the bladder region. The ultrasound signal is in the form of a series of signal bursts, known as scanlines, in successive scanplanes, the scanplanes being separated by a specific angle. In the embodiment shown, each scanplane comprises approximately 65 individual scanlines, although this can be varied depending upon the particular embodiment. A single scanplane is shown in FIG. 2 for illustration.

After one plane (one scanplane) of ultrasound scanlines is transmitted, the transducer 10 is rotated through a small angle θ and another plane of signals is transmitted, the second plane being thus slightly rotated from the first plane. In the embodiment shown, successive scanplanes are separated by approximately 15°, although this can be varied. A total of 12 such scanlines are typically produced, covering a total of 180°.

The returning scanline signals from the bladder are received by transducer 10 and directed to the microprocessor 12, for determination of the actual volume of the bladder. This volume determination process is also described in detail in the '871 and '985 patents. This value is referred to herein as an actual volume value, or volume$_{actual}$.

The combination of a plurality of scanplanes, with each scanplane comprising a number of individual scanlines, results in a solid angle scan cone. Each scanline spatially samples a particular segment of the overall image cone. The scanlines in total completely sample the image cone and define the image cone boundaries. As indicated above, the scanlines cover a 15° angle in successive planes. In spherical coordinates, each scanline has a phi ($\phi$) angle value (between adjacent scanlines) in a given scanplane and a theta ($\theta$) scanplane angle value, as well as front and back bladder wall axial locations. The angles $\phi$ and $\theta$ thus describe the location of each scanline relative to the bladder.

The present invention uses the concept of a "spherical wedge" volume, associated with each scanline which extends through the bladder. These spherical wedges in total define the entire volume of the bladder, as well as the surface area of the bladder. The surface area of the bladder is determined in the present invention using the surfaces of those wedges. The resulting surface area of the bladder is used in the determination of what is referred to herein as a normalized surface area index. More specific information on the determination of bladder surface area is provided below.

In the present invention, the normalized surface area index is a number which is specifically related to the roundness of the bladder which, as indicated above, is a reliable indication of fullness of the bladder and hence the resulting pressure of urine within the bladder. This normalized surface area index value is determined by the inventors herein to be the value of the surface area of the bladder calculated from the volume measurement as if the bladder were perfectly round, i.e. a perfect sphere, for that particular volume (this value is referred to as surface area$_{theoretical}$) divided by the surface area of the bladder calculated from the actual ultrasound signals (referred to herein as surface area$_{actual}$). Typically, the numerator (surface area$_{theoretical}$) of the index value will change as the bladder fills, while the denominator (surface area$_{actual}$) will remain constant.

The surface area$_{theoretical}$ value is derived using the bladder volume value obtained by conventional calculations, such as described in the '871 and '985 patents. The surface area of a perfect sphere using that volume is then calculated. This is of course readily accomplished through known geometric formulas. The formula for the volume of a sphere is: $V = \frac{4}{3}\pi R^3$, where R is the radius of the sphere. With the known volume, the above formula is solved for R. Once R is known, then the surface area of the perfect sphere with that radius is calculated using the conventional formula: $A = \pi R^2$. The numerator of the normalized surface area index value is now known.

The denominator of the index value is the actual value of surface area of the bladder, calculated from the ultrasound signal information. The actual surface area is determined using the "spherical wedge" concept described above. Successive spherical wedges are defined by the front and back walls of the bladder, the adjacent spherical wedges in the same scanplane, separated by angle phi and adjacent spherical wedges from adjacent scanplanes, separated by angle theta. For the following calculations, each scanline has associated therewith an imaginary spherical wedge and each scanline is assumed to pass through the geometric center of the imaginary spherical wedge associated therewith.

Figure 3:
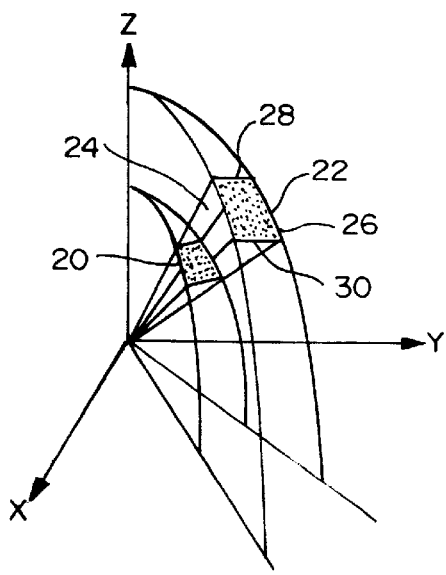
FIG. 3 shows a "wedge" portion of the bladder for one scanline.

One spherical wedge is shown for illustration in FIG. 3. The spherical wedge includes a top or front wall 20 of the bladder (nearest the transducer 10) and a bottom or back wall 22. Both of these are surface area portions of the bladder. The west and east surfaces 24 and 26 are the surfaces defined by adjacent scanplanes, while surfaces 28 and 30 are the surfaces defined by adjacent scanlines in a single scanplane. This spherical wedge concept is used in the calculation of the surface area of the bladder from the actual ultrasound signal information. This resulting value is the index value denominator, surface area$_{actual}$.

The volume of the bladder using a compilation of all of the imaginary spherical wedges in the bladder is as follows:

Volume=⅓[cos(phi$_1$)−cos(phi$_2$)][theta$_2$−theta$_1$] [$R_2^3$−$R_1^3$]

For the top side surface area of the wedge, i.e. the surface area 20 at the front of the bladder, the surface area calculation is as follows:

Top side=$R_2^2$ [cos(phi$_1$)−cos(phi$_2$)][theta$_2$−theta$_1$]

The bottom side surface area of the wedge, i.e. the back wall surface area, is:

Bottom side=$R_1^2$[cos(phi$_1$)−cos(phi$_2$)][theta$_2$−theta$_1$]

The above equations are appropriate for the top and bottom surface area calculations for all the scanlines, except the broadside scanline, which is at the center, at phi ($\phi$)=0. For this scanline, the surface areas for the top and bottom is counted only once. A modified formula for the broadside scanline is based on a truncated cone, with the volume, top and bottom area calculations being as follows:

$$\text{Volume} = \frac{\pi}{3}\tan^2(phi)[R_2^3 - R_1^3]$$

while the bottom side surface area is:

Bottom side=$\pi R_2^2$ tan$^2$(phi)

and the top side surface is:

Top side=$\pi R_1^2$ tan$^2$(phi)

Referring now again to FIG. 3, the west side surface 40 of the spherical wedge is:

West side=½(theta$_2$−theta$_1$) ($R_2^2$−$R_1^2$)

the east side surface 42 is:

East side=½(theta$_2$−theta$_1$) ($R_2^2$−$R_1^2$)

the north side surface 44 is:

North side=½(phi$_2$−phi$_1$) ($R_2^2$−$R_1^2$)

and the south side surface 46 is:

South side=½(phi$_2$−phi$_1$) ($R_2^2$−$R_1^2$)

Figure 4:
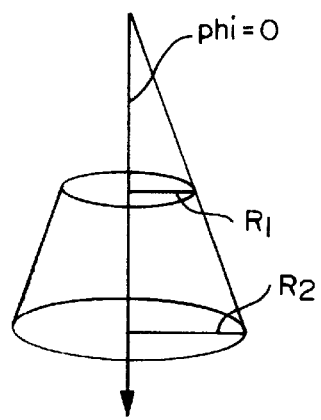
FIG. 4 shows a truncated cone for a broadside scanline.
Figure 5:
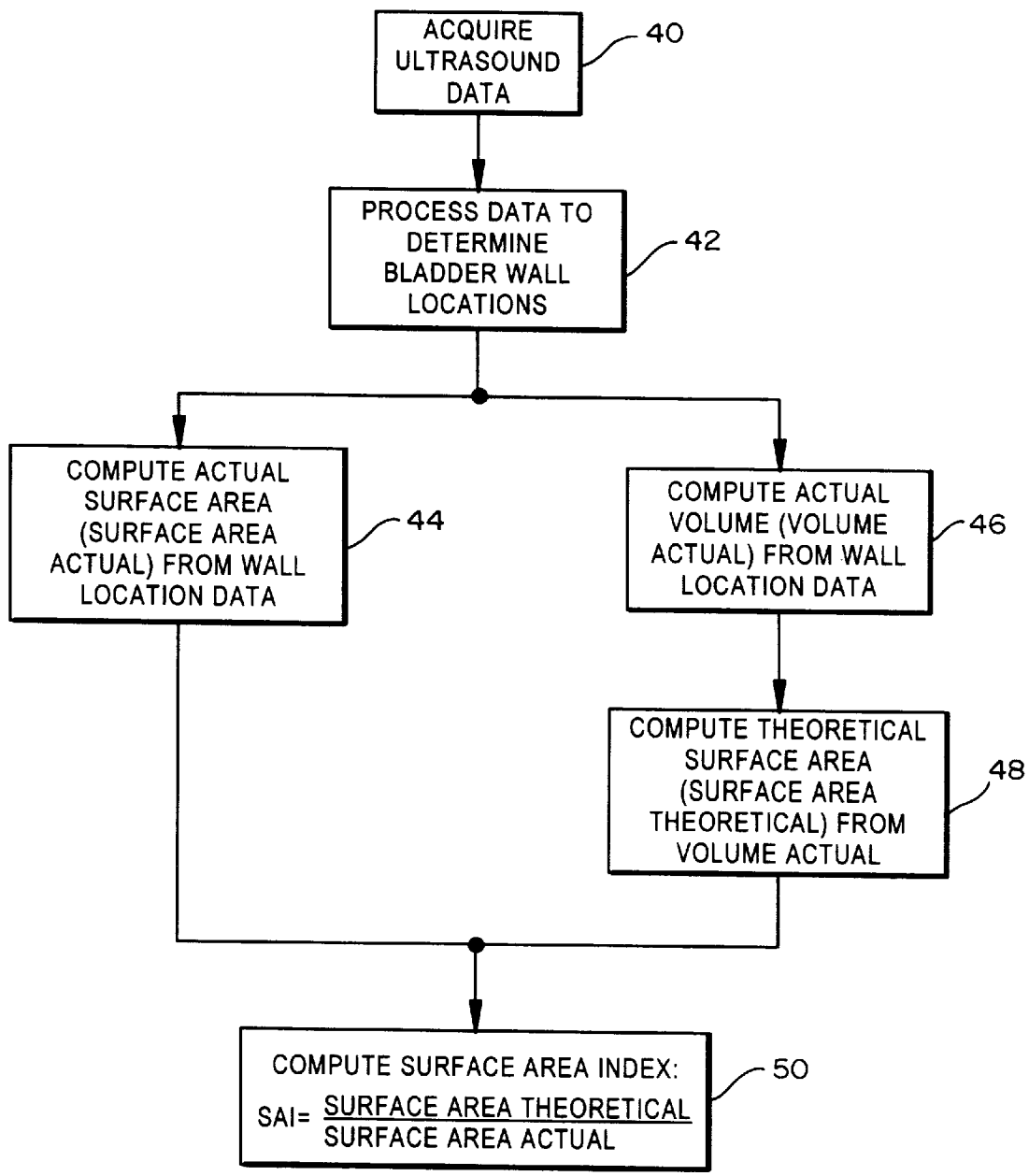
FIG. 5 is a flow chart showing the processing steps in the present invention.

The corresponding side contributions for the broadside scanline of FIG. 4 are divided by the number of scanplanes (12 in the embodiment shown). Hence, the side would be added for each scanplane where the lateral edge of the bladder ends on the broadside scanline.

Substituting the above information into the normalized surface equation above provides the following result: Normalized surface area=$4\pi[\frac{3}{4}\pi \cdot \text{vol}_{actual}]^{2/3}$/surface area$_{actual}$. The numerator value is surface area$_{theoretical}$ discussed above.

FIG. 4 shows a flow chart for the operation of the system of the present invention. First, ultrasound data is acquired relative to the bladder, as shown in block 40. Then, the ultrasound data is processed to determine the locations of the bladder walls, as shown in block 42. Again, these two steps are disclosed in the '871 and '985 patents. The processed data is then used to determine actual surface area, as shown in block 44. Further, an actual volume value is determined from the processed information, as shown at block 46.

From the volume information (block 46), the theoretical surface area is calculated of a sphere having that volume, as shown in block 48. The surface area index (SAI) is then determined (block 50) by dividing the calculated actual surface area value from block 44 into the theoretical surface area determined from block 48.

The significance of the normalized surface index (referred to hereinafter as surface area index or SAI) will now likely be apparent to those skilled in the art. As the index value approaches one, the bladder is in fact becoming rounder and rounder, i.e. more like the theoretical perfect sphere. This means that the bladder is becoming more completely filled, with a resulting increase in pressure. Reaching specific points in the index can be used to initiate preselected actions, including various appropriate warnings to the user, including an indication as to an appropriate time to void. Potentially dangerous conditions, such as overfilling, with resulting distension, can be accurately predicted in advance and thus avoided.

Hence, the apparatus of the present invention can be used as an accurate diagnostic tool, but it can also be used as a therapeutic tool to assist in training of people with bladder dysfunction. When the index reaches selected levels, warnings can be provided to the user in various ways, including an auditory alarm, a visual alarm or a kinetic alarm, such as a vibration. Further, an alarm may be transmitted to a remote location, such as a nursing station, either by a wire or wireless (RF) communication link.

Although a preferred embodiment of the invention has been disclosed herein for illustration, it should be understood that various changes, modifications and substitutions may be incorporated in such embodiment without departing from the spirit of the invention, which is defined by the claims as follows.

What is claimed is:

1. An apparatus for automatically determining a bladder volume index value, which provides information concerning bladder condition of a user, comprising:

means for automatically scanning a bladder of a user with ultrasound signals, receiving the returning signals, and calculating therefrom the volume of urine in the bladder;

means for automatically calculating an actual surface area of the user's bladder from said returning ultrasound signals;

means for automatically determining a theoretical surface area of a sphere having said calculated volume; and means for determining a surface area index value for the user as follows:

$$\frac{\text{Surface area (theoretical)}}{\text{Surface area (actual)}} = \text{Surface area index } (SAI).$$

2. An apparatus of claim 1, including means for securing the apparatus to the person of a user.

3. An apparatus of claim 1, including means for storing said values of SAI over time.

4. An apparatus of claim 1, including means for storing said values of actual surface area of the bladder over time.

5. An apparatus of claim 1, including means for generating an alarm to the user when the SAI reaches a selected level.

6. An apparatus of claim 5, wherein the alarm is auditory.

7. An apparatus of claim 5, wherein the alarm is visual.

8. An apparatus of claim 5, wherein the alarm is kinetic.

9. An apparatus of claim 5, including means for transmitting the alarm to a remote location.

10. An apparatus of claim 9, wherein the transmitting means is wireless.

11. An apparatus of claim 1, wherein the surface area calculation includes the following calculations for each ultrasound scanline signal:

$$\text{Top side} = R_2^2 \, [\cos(phi_1) - \cos(phi_2)][theta_2 - theta_1]$$

$$\text{Bottom side} = R_1^2 \, [\cos(phi_1) - \cos(phi_2)][theta_2 - theta_1]$$

$$\text{West side} = \tfrac{1}{2}(theta_2 - theta_1)(R_2^2 - R_1^2)$$

$$\text{East side} = \tfrac{1}{2}(theta_2 - theta_1)(R_2^2 - R_1^2)$$

$$\text{North side} = \tfrac{1}{2}(phi_2 - phi_1)(R_2^2 - R_1^2)$$

$$\text{South side} = \tfrac{1}{2}(phi_2 - phi_1)(R_2^2 - R_1^2)$$

Where $R_1$=distance to front wall of the bladder, $R_2$=distance to the rear wall of the bladder, $theta_1$ and $theta_2$=adjacent scanplane angles, and $phi_1$ and $phi_2$=adjacent scanline angles.

12. A method for automatically determining a bladder volume index value, which provides information concerning the bladder condition of a user, comprising the steps of:

automatically scanning a bladder of a user with ultrasound signals, receiving the returning signals and calculating therefrom the volume of urine in the bladder;

automatically calculating an actual surface area of the user's bladder from the returning ultrasound signals;

automatically determining a theoretical surface area of a sphere having said calculated volume; and determining a surface area index value for the user as follows:

$$\frac{\text{Surface area (theoretical)}}{\text{Surface area (actual)}} = \text{Surface area index } (SAI).$$

13. A method of claim 12, including the step of storing said values of SAI over time.

14. A method of claim 12, including the step of generating an alarm to the user when the SAI reaches a selected level.

15. A method of claim 14, wherein the alarm is auditory.

16. A method of claim 14, wherein the alarm is visual.

17. A method of claim 14, wherein the alarm is kinetic.

18. A method of claim 14, including the step of transmitting the alarm to a remote location.

* * * * *